United States Patent
Sparklin et al.

(10) Patent No.: US 10,219,544 B2
(45) Date of Patent: Mar. 5, 2019

(54) AEROSOL DELIVERY DEVICE AND A RELATED METHOD

(71) Applicant: RAI Strategic Holdings, Inc., Winston-Salem, NC (US)

(72) Inventors: Eric M. Sparklin, Greensboro, NC (US); Sawyer A. Hubbard, Winston-Salem, NC (US); Karen V. Taluskie, Winston-Salem, NC (US); Stephen Benson Sears, Siler City, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 0 days.

(21) Appl. No.: 15/468,883

(22) Filed: Mar. 24, 2017

(65) Prior Publication Data
US 2018/0271150 A1    Sep. 27, 2018

(51) Int. Cl.
| A24F 47/00 | (2006.01) |
| H05B 6/80 | (2006.01) |
| A24F 1/30 | (2006.01) |
| A61M 15/06 | (2006.01) |
| B65D 81/34 | (2006.01) |
| H05B 6/64 | (2006.01) |

(52) U.S. Cl.
CPC .............. *A24F 47/008* (2013.01); *A24F 1/30* (2013.01); *A61M 15/06* (2013.01); *H05B 6/802* (2013.01); *B65D 81/3446* (2013.01); *H05B 6/64* (2013.01)

(58) Field of Classification Search
CPC .................................................... A24F 47/008
See application file for complete search history.

(56) References Cited

U.S. PATENT DOCUMENTS

| 4,793,365 A | 12/1988 | Sensabaugh, Jr. et al. |
| 4,922,901 A | 5/1990 | Brooks et al. |
| 4,947,874 A | 8/1990 | Brooks et al. |
| 4,947,875 A | 8/1990 | Brooks et al. |

(Continued)

FOREIGN PATENT DOCUMENTS

| GB | 2 524 779 | 10/2015 |
| WO | WO 98/57556 | 12/1998 |

(Continued)

OTHER PUBLICATIONS

Chemical and Biological Studies on New Cigarette Prototypes that Heat Instead of Burn Tobacco, RJRTC Monograph, 1988.

*Primary Examiner* — James Harvey
(74) *Attorney, Agent, or Firm* — Womble Bond Dickinson (US) LLP

(57) ABSTRACT

The present disclosure relates to an aerosol delivery device and a related method. The aerosol delivery device includes a heating chamber having an aerosol precursor composition disposed therein. A microwave radiation emitting device is operably engaged with the heating chamber and is configured to heat the aerosol precursor composition therein with the microwave radiation to form an aerosol from the aerosol precursor composition. An outlet port is formed in a housing of the aerosol delivery device and is in fluid communication with the heating chamber. The heating chamber is responsive to a suction applied to the outlet port for the aerosol to be drawn through the outlet port outwardly from the housing.

32 Claims, 8 Drawing Sheets

(56) References Cited

U.S. PATENT DOCUMENTS

| | | | |
|---|---|---|---|
| 5,101,839 A | 4/1992 | Jakob et al. | |
| 5,261,424 A | 11/1993 | Sprinkel, Jr. et al. | |
| 5,372,148 A | 12/1994 | McCafferty et al. | |
| 5,934,289 A | 8/1999 | Watkins et al. | |
| 5,954,979 A | 9/1999 | Counts et al. | |
| 5,967,148 A | 10/1999 | Harris et al. | |
| 6,040,560 A | 3/2000 | Fleischhauer et al. | |
| 6,803,545 B2 | 10/2004 | Blake et al. | |
| 7,040,314 B2 | 5/2006 | Nguyen et al. | |
| 7,293,565 B2 | 11/2007 | Griffen et al. | |
| 7,726,320 B2 | 6/2010 | Robinson et al. | |
| 8,402,976 B2 | 3/2013 | Fernando et al. | |
| 8,689,804 B2 | 4/2014 | Fernando et al. | |
| 8,881,737 B2 | 11/2014 | Collett | |
| 9,072,322 B2 | 7/2015 | Liu | |
| 2004/0232144 A1* | 11/2004 | Edmark | A47J 36/027 219/735 |
| 2009/0151717 A1* | 6/2009 | Bowen | A61M 11/041 128/200.23 |
| 2010/0313901 A1* | 12/2010 | Fernando | A24F 47/008 131/330 |
| 2011/0139669 A1* | 6/2011 | Huppert | A24F 25/00 206/524.1 |
| 2013/0255702 A1 | 10/2013 | Griffith, Jr. et al. | |
| 2014/0000638 A1* | 1/2014 | Sebastian | A24F 47/008 131/328 |
| 2014/0065265 A1* | 3/2014 | Lestage | B65D 81/3469 426/87 |
| 2014/0096781 A1 | 4/2014 | Sears et al. | |
| 2016/0331913 A1* | 11/2016 | Bourque | A61M 11/02 |
| 2017/0021026 A1* | 1/2017 | Naheed | A61K 47/36 |
| 2017/0157106 A1* | 6/2017 | Rogers | A24B 13/00 |
| 2017/0164655 A1* | 6/2017 | Chen | A24F 47/008 |
| 2017/0202266 A1* | 7/2017 | Sur | A24F 47/008 |
| 2017/0251718 A1* | 9/2017 | Armoush | A24F 1/30 |
| 2017/0273495 A1* | 9/2017 | Choueiri | A47J 27/004 |

FOREIGN PATENT DOCUMENTS

| | | |
|---|---|---|
| WO | WO 2007/024130 | 3/2007 |
| WO | WO 2010/003480 | 1/2010 |
| WO | WO 2016/135224 | 9/2016 |
| WO | WO 2016/200815 | 12/2016 |

\* cited by examiner

500 ↘

502 — OPERABLY ENGAGING A MICROWAVE RADIATION EMITTING DEVICE WITH A HEATING CHAMBER CONFIGURED TO RECEIVE AN AEROSOL PRECURSOR COMPOSITION THEREIN, THE MICROWAVE RADIATION EMITTING DEVICE BEING CONFIGURED TO HEAT THE AEROSOL PRECURSOR COMPOSITION WITH MICROWAVE RADIATION EMITTED THEREBY TO FORM AN AEROSOL FROM THE AEROSOL PRECURSOR COMPOSITION

504 — ENGAGING THE HEATING CHAMBER WITH A HOUSING HAVING AN OUTLET PORT SUCH THAT THE OUTLET PORT IS IN FLUID COMMUNICATION WITH THE HEATING CHAMBER, AND SUCH THAT THE HEATING CHAMBER IS RESPONSIVE TO A SUCTION APPLIED TO THE OUTLET PORT FOR THE AEROSOL TO BE DRAWN THROUGH THE OUTLET PORT OUTWARDLY FROM THE HOUSING

FIG. 5

AEROSOL DELIVERY DEVICE AND A RELATED METHOD

FIELD OF THE DISCLOSURE

The present disclosure relates to aerosol delivery devices, and more particularly to a microwave radiation heating element configured to heat an aerosol precursor composition, made or derived from tobacco or otherwise incorporating tobacco-related material, to form an inhalable substance for human consumption.

BACKGROUND

Smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco.

To this end, there have been proposed smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 8,881,737 to Collett et al. and U.S. Pat. No. 7,726,320 to Robinson et al., U.S. Pat. App. Pub. Nos. 2013/0255702 to Griffith, Jr. et al.; 2014/0000638 to Sebastian et al.; and 2014/0096781 to Sears et al., which are incorporated herein by reference.

Of these smoking products, flavor generators, and medicinal inhalers that employ electrical energy to produce heat for smoke or aerosol formation, a wick and coil arrangement is often utilized in conjunction with an electrical power source, such as a battery. More particularly, in this arrangement, the coil is in direct contact with the wick and acts as a heating element. The coil is configured to conduct electrical current from the battery, and heat, by direct contact, a limited quantity of aerosol precursor composition absorbed by the wick. However, a wick and coil arrangement may cause thermal degradation of the aerosol precursor composition since direct heating may result in uneven heating of the aerosol precursor composition.

Accordingly, it is desirable to provide an aerosol delivery device that employs heat produced by an external energy source to heat an aerosol precursor composition to provide the sensations of cigarette, cigar, or pipe smoking, which preferably does so without direct contact with or thermal degradation of the aerosol precursor composition, in order to prolong the service life of the device and deliver a more consistent aerosol.

BRIEF SUMMARY OF THE DISCLOSURE

The present disclosure relates to aerosol delivery devices configured to produce aerosol for human consumption. In one aspect, an aerosol delivery device comprises a heating chamber having an aerosol precursor composition disposed therein, a microwave radiation emitting device operably engaged with the heating chamber, and configured to heat the aerosol precursor composition therein with the microwave radiation, to form an aerosol from the aerosol precursor composition, and a housing having an outlet port and being in fluid communication with the heating chamber, the heating chamber being responsive to a suction applied to the outlet port for the aerosol to be drawn through the outlet port outwardly from the housing.

In another aspect, a method of making an aerosol delivery device comprises operably engaging a microwave radiation emitting device with a heating chamber configured to receive an aerosol precursor composition therein, the microwave radiation emitting device being configured to heat the aerosol precursor composition with microwave radiation emitted thereby to form an aerosol from the aerosol precursor composition, and engaging the heating chamber with a housing having an outlet port such that the outlet port is in fluid communication with the heating chamber, and such that the heating chamber is responsive to a suction applied to the outlet port for the aerosol to be drawn through the outlet port outwardly from the housing.

BRIEF DESCRIPTION OF THE FIGURES

Figure 1:
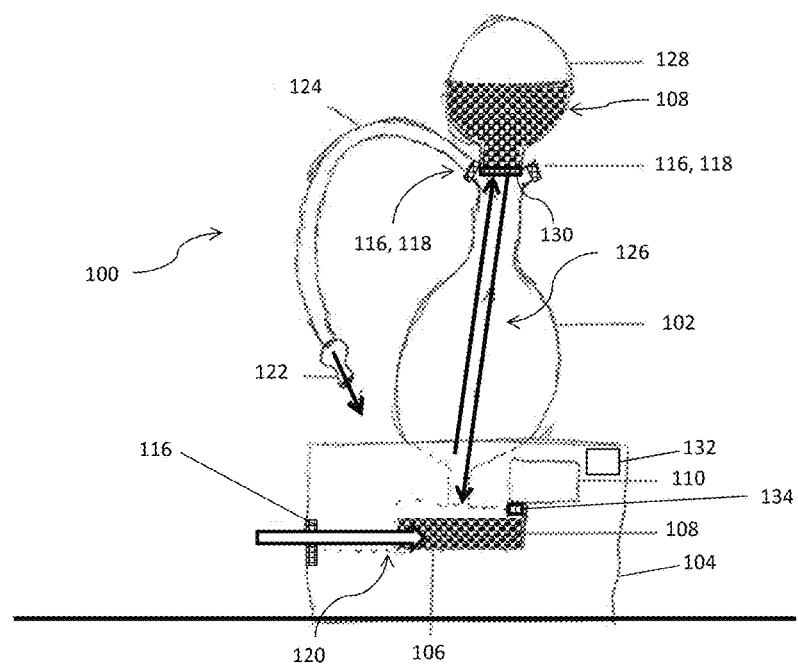
Figure 2A:
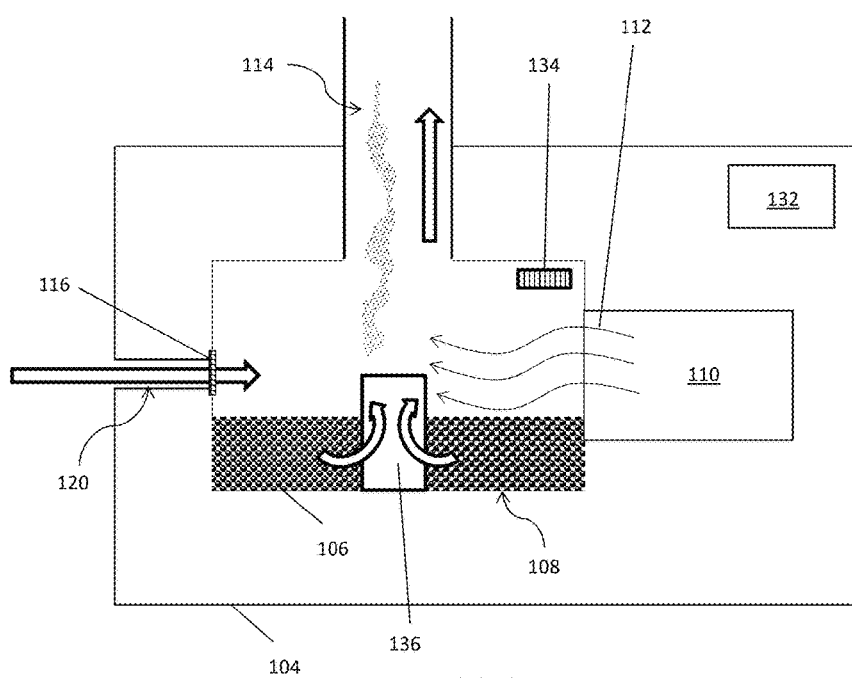
Figure 2B:
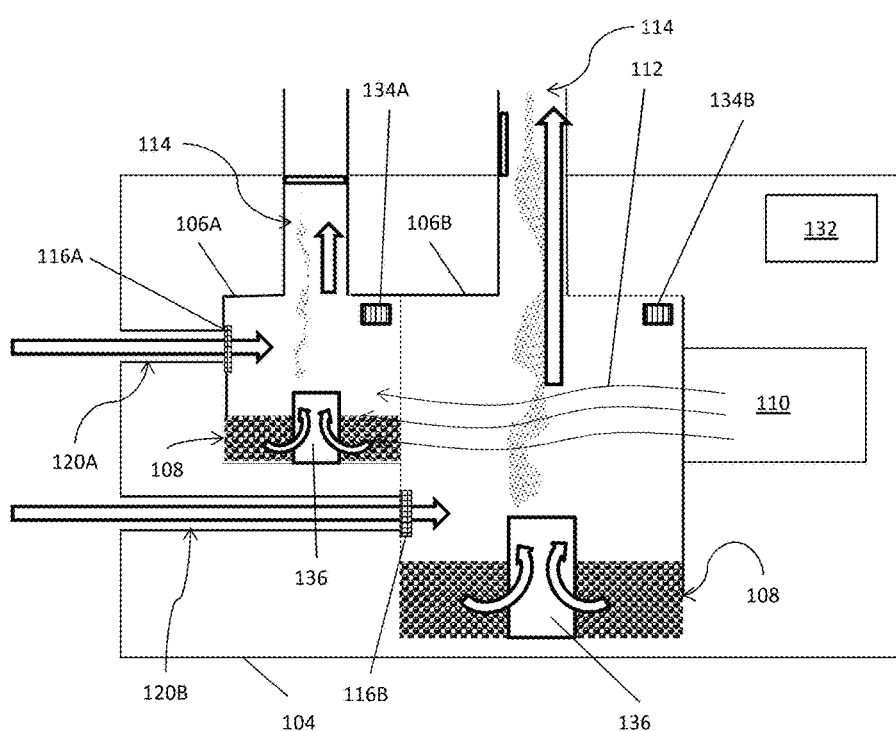
Figure 3:
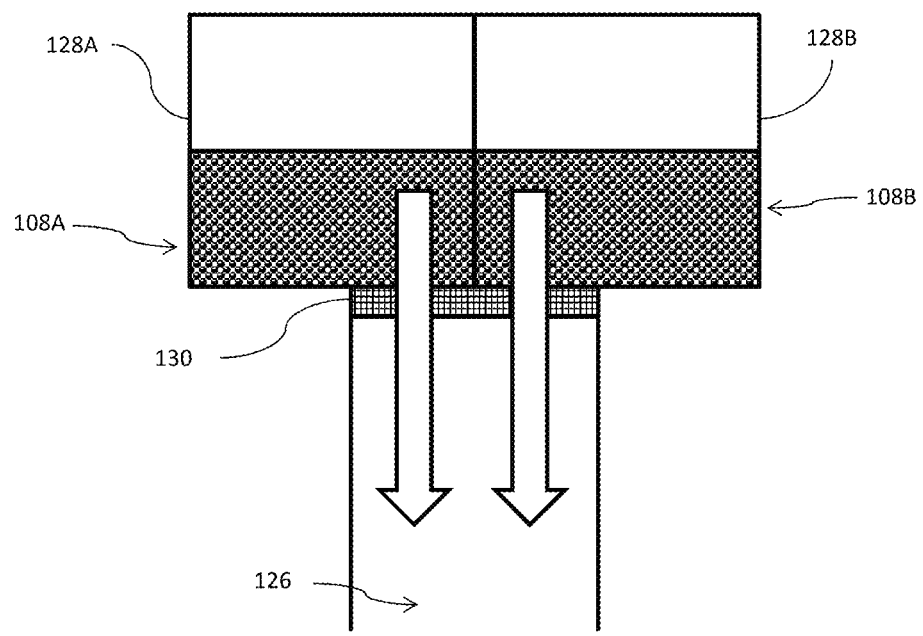
Figure 4A:
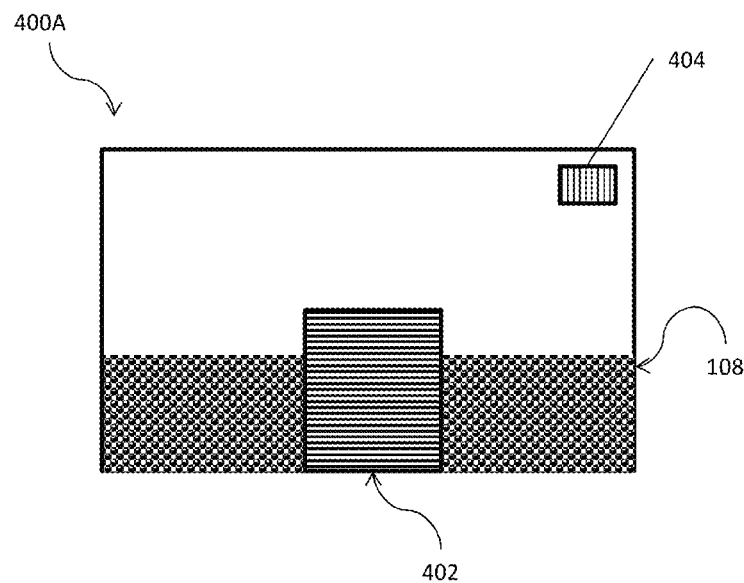
Figure 4B:
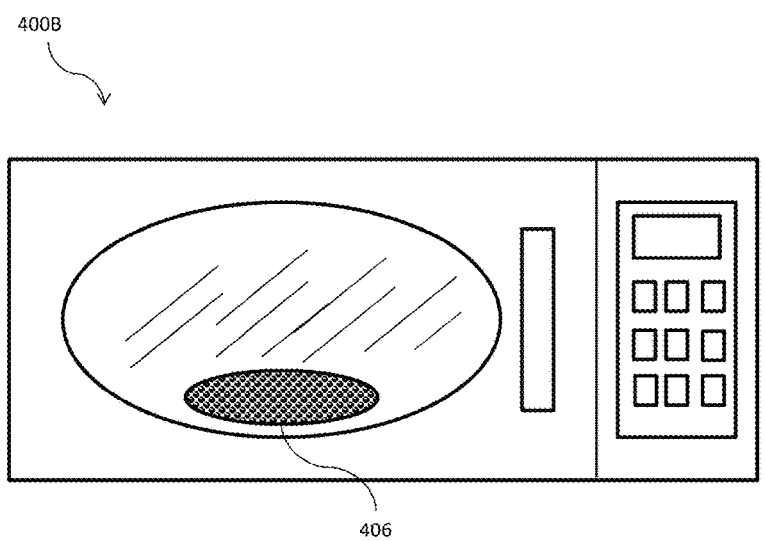
Figure 4C:
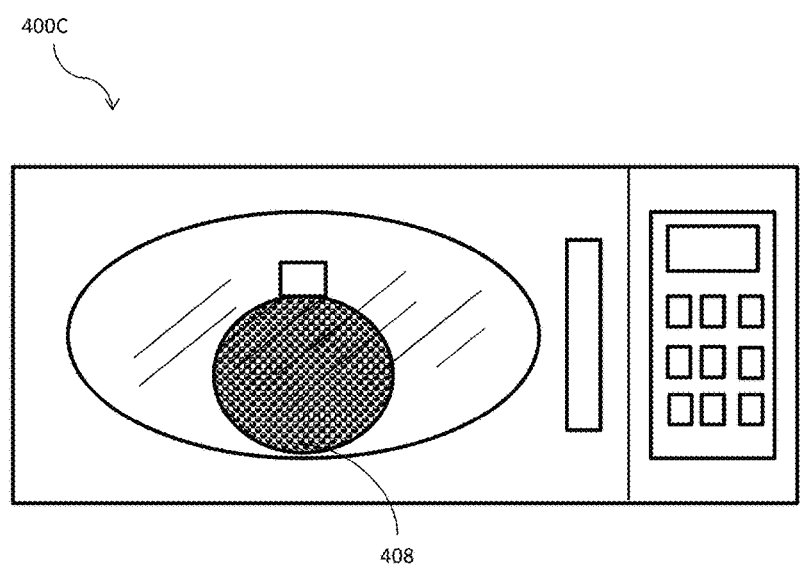

Having thus described the disclosure in the foregoing general terms, reference will now be made to the accompanying drawings, which are not necessarily drawn to scale, and wherein:

FIG. 1 illustrates a side view of an aerosol delivery device including a microwave radiation emitting device according to an example embodiment of the present disclosure;

FIG. 2A illustrates a cross-sectional view of an aerosol produced in a heating chamber of an aerosol delivery device from microwave radiation generated by a microwave radiation emitting device according to an example embodiment of the present disclosure;

FIG. 2B illustrates a cross-sectional view of aerosol produced in two heating chambers of an aerosol delivery device from microwave radiation generated by a microwave radiation emitting device according to an example embodiment of the present disclosure;

FIG. 3 illustrates a cross-sectional view of aerosol precursor compositions in two different reservoirs of an aerosol delivery device according to an example embodiment of the present disclosure;

FIGS. 4A-C illustrate aerosol precursor processing devices according to example embodiments of the present disclosure; and FIG. 5 illustrates a flow diagram of a method of making an aerosol delivery device according to example embodiments of the present disclosure.

DETAILED DESCRIPTION OF PREFERRED EMBODIMENTS

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present disclosure relates to aerosol delivery devices that use microwave radiation to heat a material (preferably without combusting the material to any significant degree) to form an inhalable substance. In some aspects, the aerosol delivery devices are considered "table top" devices, similarly configured in size, shape, etc., to that of a conventional hookah. However, in other aspects, the aerosol delivery devices are considered "hand-held" devices and are sized, shaped, etc., to be easily held in the hands of consumers.

In certain preferred embodiments, the aerosol delivery devices are characterized as smoking articles. As used herein, the term "smoking article" is intended to mean an article or device that provides some or all of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe, without any substantial degree of combustion of any component of that article or device. As used herein, the term "smoking article" does not necessarily mean that, in operation, the article or device produces smoke in the sense of the aerosol resulting from by-products of combustion or pyrolysis of tobacco, but rather, that the article or device yields vapors (including, e.g., vapors within aerosols that can be considered to be visible aerosols that might be considered to be described as smoke-like) resulting from volatilization or vaporization of certain components of the article or device. In some preferred embodiments, the articles or devices characterized as smoking articles incorporate tobacco and/or components derived from tobacco.

In various aspects, articles or devices of the present disclosure are also characterized as being vapor-producing articles, aerosol delivery articles, or medicament delivery articles. Thus, such articles or devices are adapted so as to provide one or more substances (e.g., flavors and/or pharmaceutical active ingredients) in an inhalable form or state. For example, inhalable substances are substantially in the form of a vapor (i.e., a substance that is in the gas phase at a temperature lower than its critical point). Alternatively, inhalable substances are in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

In use, smoking articles of the present disclosure are subjected to many of the physical actions employed by an individual in using a traditional type of smoking article (e.g., a cigarette, cigar, or pipe that is employed by lighting and inhaling tobacco). For example, the user of a smoking article of the present disclosure manipulates that article much like a traditional type of smoking article, draws on one mouthpiece element of that article for inhalation of aerosol produced by that article, takes puffs at selected intervals of time, etc.

Smoking articles of the present disclosure comprise some combination of a heat source (i.e., a microwave radiation-emitting element), at least one control component (e.g., arrangement for actuating, controlling, regulating and/or ceasing power to the heat source for controlling heat generation, such as by controlling microwave radiation emitted from the heat source to other components of the smoking article), an aerosol precursor composition (e.g., commonly a liquid capable of yielding an aerosol upon application of sufficient heat, such as ingredients commonly referred to as "smoke juice," "e-liquid" and "e-juice"), and a mouthpiece element for allowing draw upon the smoking article (otherwise referred to herein as an aerosol delivery device) for aerosol inhalation (e.g., a defined air flow path through the smoking article such that aerosol generated can be withdrawn therefrom upon draw).

One example embodiment of an aerosol delivery device 100 is provided in FIG. 1. As seen in the side view illustrated therein, the aerosol delivery device 100 comprises a housing 102 and an enclosure 104 that are either permanently or detachably connected in a functioning relationship. The enclosure 104 is configured in size and/or shape to fit around a first portion of the housing 102 and to substantially enclose the first portion of the housing 102 therein. In some instances, the first portion is a lower portion or base of the housing 102. For example, the enclosure 104 is molded to correspond to external contours of the first portion of the housing 102 and is hinged to open and close. In this manner, the first portion of the housing 102 is fit into the molded contour of the enclosure 104 when the enclosure is hingedly opened and is fixedly retained within when the enclosure is hingedly closed. Other types of engagement or connection between the housing 102 and the enclosure 104 are also contemplated.

In one embodiment, a heating chamber 106 configured to receive an aerosol precursor composition 108 therein defines the first portion of the housing 102. In some aspects, the enclosure 104 substantially surrounds or encloses the heating chamber 106. The heating chamber 106 is a single heating chamber or, in some embodiments, is divided into further sub-chambers. For example, in one embodiment as illustrated in FIG. 1 and in more detail in FIG. 2A, a single heating chamber 106 is provided. In another example, as another embodiment illustrated in FIG. 2B, a first heating sub-chamber 106A and a second heating sub-chamber 106B are provided. In such instances, one of the first and second heating sub-chambers 106A-B is configured as having a greater capacity for the aerosol precursor composition 108 than the other sub-chamber. In the example illustrated in FIG. 2B, the second heating sub-chamber 106B has a greater capacity for the aerosol precursor composition 108 than the first heating sub-chamber 106A. In other such instances, the first and second heating sub-chambers 106A-B are configured as having a substantially similar capacity for the aerosol precursor composition 108.

In either instance, the heating chamber 106 is operably engaged with a heat source, such as a microwave radiation emitting device 110. The microwave radiation emitting device 110 comprises, in some aspects, a magnetron that generates microwave radiation 112. In some aspects, the magnetron is preferably sized to conform to a desired shape, size, etc., of the aerosol delivery device 100 so that the device is easily manipulated, without detracting from a desirable smoking experience. In other aspects, the microwave radiation emitting device 110 comprises an antenna, coils, or the like, configured to generate the microwave radiation 112. In such cases the material to be heated may reside in different arrangement/orientation with respect to the microwave source. For example in the case of a coil, the material may reside in the interior (center) of the coil.

As such, the microwave radiation 112 emitted by the microwave radiation emitting device 110 is configured to penetrate the heating chamber 106 and heat the aerosol precursor composition 108 disposed therein in order to form an aerosol 114 therefrom. More particularly, in some aspects, the microwave radiation 112 induces polar molecules of the aerosol precursor composition 108 to rotate and produce thermal energy. Consequently, the molecules in the aerosol precursor composition are excited and heated by the microwave radiation 112 in a uniform manner so that minimal thermal degradation (i.e., there are no superheated particles) of the aerosol precursor composition 108 occurs upon the formation of the aerosol 114, and the resulting aerosol 114 has a more consistent vapor chemistry than that produced by other types of heat sources, such as electric heating elements (e.g., a resistive heating coil).

In some aspects, the microwave radiation emitting device 110, as well as other aspects of the aerosol delivery device 100, itself, is electrically powered by a power source. The power source is configured to provide power, energy, or current flow sufficient to provide various functionalities of the aerosol delivery device 100, such as heating of the aerosol precursor composition via the microwave radiation emitting device 110, powering of control components or systems, powering of indicators, and the like. Preferably, the power source can take on various embodiments that are each capable of delivering sufficient power to the microwave radiation emitting device 110 to rapidly heat the aerosol precursor composition 108 received in the heating chamber 106 for forming the aerosol therefrom, and to power other components of the aerosol delivery device 100 through use for the desired duration of time. For example, in some instances, the aerosol delivery device 100, including the microwave radiation emitting device 110, is powered via a standard household outlet (e.g., 120 AC volts). In another example, the aerosol delivery device 100 is powered by a battery of a sufficient energy density. Therefore, when the aerosol delivery device 100 is connected to a power source, the microwave radiation emitting device 110 is powered and controllable to heat the aerosol precursor composition 108 disposed in the heating chamber 106.

The housing 102, the enclosure 104, and/or the heating chamber 106 are configured such that the microwave radiation 112 emitted by the microwave radiation emitting device 110 is contained therein. For example, the housing 102, the enclosure 104, and/or the heating chamber 106 are similar in materials and design to a Faraday cage to prevent the microwave radiation from escaping or leaking out. Any outlet port or orifice extending through a surface of the housing 102, the enclosure 104, and/or the heating chamber 106, and in fluid communication with an exterior of the housing 102 or enclosure 104, includes a shielding element 116 to contain the microwave radiation 112 within the aerosol delivery device 100. In these aspects, the housing 102 of the aerosol delivery device 100 defines the outlet port 118, and the outlet port 118 is in fluid communication with the heating chamber 106. As such, a shielding element 116 is engaged with the outlet port 118. An airflow channel 120 defined within the housing 102 and/or the enclosure 104 also includes a shielding element 116. The shielding element 116 comprises at least one layer of a conductive material (e.g., an aluminum mesh), although other materials, types, and/or configurations of a shielding element 116 are contemplated.

The outlet port 118 is configured to receive suction (i.e., from a consumer) at a mouthpiece element 122, such that the aerosol 114 is drawn through the outlet port 118 outwardly from the housing 102 in response to the suction. A hose member 124 is engageable with the outlet port 118. As illustrated in FIG. 1, for example, a proximal end of the hose member 124 is engaged with the outlet port 118 and an opposing distal end is engaged with the mouthpiece element 122. In this manner, the mouthpiece element 122 and the hose member 124 are in fluid communication with the heating chamber 106 via the outlet port 118 so as to receive the aerosol 114 therefrom in response to suction applied to the mouthpiece element 122. In some aspects, there is more than one outlet port 118. For example and as illustrated in FIG. 1, there are at least two outlet ports 118. In such instances, a hose member 124 with a mouthpiece element 122 is engaged with each available outlet port 118 of the housing 102, such that multiple consumers are able to use the aerosol delivery device 100 at one time. Otherwise, unused outlet ports are configured to be capped or blocked off to prevent the aerosol from escaping from the housing 102 therethrough or otherwise from entering and diluting the aerosol in the housing 102.

In some aspects, the one or more heating sub-chambers 106A-B are configured to be selectively in fluid communication with a respective outlet port 118. For example, a selector element (e.g., a valve, flange) disposed within the one or more heating sub-chambers 106A-B is configured to be automatically responsive to the suction applied through the outlet port 118 to direct the aerosol 114 through the outlet port 118 from a respective heating sub-chamber 106A-B. FIG. 2A illustrates such an example, where the selector element is responsive or opens the second heating sub-chamber 106B in response to suction applied through a respective outlet port. In FIG. 2A, for example, as the outlet port through which suction is applied is not engaged with the first heating sub-chamber 106A, the selector element is nonresponsive or closed, such that no aerosol 114 is directed therefrom.

In other examples, the selector element is configured to be manually responsive to user selection. In these instances, a switch, button, lever, or any other mechanism is usable to selectively control from which heating sub-chamber 106A-B the aerosol 114 is directed.

The airflow channel 120 is configured to allow airflow between the heating chamber 106 and ambient air external to the housing 102 and/or the enclosure 104. For example, as illustrated in FIG. 1 and in more detail in FIG. 2A, a single heating chamber 106 has an airflow channel 120 extending from an interior of the heating chamber 106, through an interior of the enclosure 104, and out to an exterior of the housing 102. In another example, as illustrated in FIG. 2B, the two heating chambers 106A-B each have an individual airflow channel 120A-B extending therefrom to the exterior of the housing 102. However, in other examples (not shown), the airflow channels 120A-B are configured to extend from a respective heating chamber 106A-B and combine into one channel within the enclosure 104, with the one channel extending to the exterior of the housing 102. In instances where there is more than one airflow channel 120, there is a shielding element 116A-B associated with each channel.

Referring back to FIG. 1, an aerosol precursor delivery arrangement 126 is in operable engagement with the heating chamber 106 and is configured to deliver the aerosol precursor composition 108 to the heating chamber 106 from a reservoir 128. The aerosol precursor delivery arrangement 126 is, in various aspects, an internal flow tube, a passageway or other mechanism. As illustrated in FIG. 1, for example, the aerosol precursor delivery arrangement 126 is an airflow passageway defined within an interior of the housing 102 and configured to direct, by gravity, the aerosol precursor composition 108 dispensed from the reservoir 128 through the housing 102 to the heating chamber 106.

In other aspects, the aerosol precursor delivery arrangement 126 is also an aerosol delivery arrangement, such that an aerosol formed by the combination of the vaporization of the aerosol precursor composition 108 and the ambient air in the heating chamber 106, is delivered to the consumer via the same mechanism that transports the aerosol precursor composition 108 to the heating chamber 106. In these aspects, the airflow passageway 126 is configured with an interior volume larger than that of the heating chamber 106 in order to provide a headspace for the produced aerosol to expand and/or age therein. In other aspects, not shown, the airflow passageway 126 is configured as a flow tube engaged between the reservoir 128 and the heating chamber 106 in order to transport the aerosol precursor composition 108 to the heating chamber 106 from the reservoir 128, as well as to provide a headspace for the produced aerosol to expand therein. Other similar mechanisms for delivering the aerosol precursor composition 108 and/or the produced aerosol are also contemplated.

The reservoir 128 is configured to contain the aerosol precursor composition 108 therein and is configured to be in fluid communication with the aerosol precursor delivery arrangement 126. FIG. 1 illustrates a reservoir 128 configured to contain a first aerosol precursor composition 108. However, in some aspects as illustrated in FIG. 3, there are two or more reservoirs 128A-B, each reservoir 128A-B being configured to contain a distinct aerosol precursor composition 108A-B therein, wherein each of the two or more reservoirs 128A-B is in fluid communication with the aerosol precursor delivery arrangement 126 and co-operable therewith.

In some aspects, for example, each of the two or more reservoirs 128A-B contains different aerosol precursor compositions 108A-B therein. In such instances, a manual or automatic actuation mechanism (not shown) is providable for selectively actuating fluid communication between one or more of the reservoirs 128A-B and the aerosol precursor delivery arrangement 126.

In other aspects, for example, each of the two or more reservoirs 128A-B contain a same or substantially similar aerosol precursor compositions 108A-B, wherein a first of the two or more reservoirs 128A is a primary reservoir and a second of the two or more reservoirs 128B is a secondary reservoir. In this instance, the first or primary reservoir 128A is configured to be in fluid communication with the aerosol precursor delivery arrangement 126, while the second or secondary reservoir 128B is configured to be in fluid communication with the aerosol precursor delivery arrangement 126 only upon depletion of the aerosol precursor composition 108A contained within the first reservoir 128A. A manual or automatic actuation mechanism (not shown) is providable in these instances in order to sense depletion of the aerosol precursor composition 108A contained within the first reservoir 128A and actuate fluid communication between the second reservoir 128B containing the aerosol precursor composition 108B and the aerosol precursor delivery arrangement 126.

The aerosol precursor delivery arrangement 126 is thereby configured to deliver either individually or in combination any of the distinct aerosol precursor compositions 108A-B from the respective one of the two or more reservoirs 128A-B to the heating chamber 106. For example, two different aerosol precursor compositions 108A-B contained within respective reservoirs 128A-B are simultaneously, but independently, delivered to respective heating sub-chambers 106A-B. In such an instance, each reservoir 128A-B is in fluid communication with an individual aerosol precursor delivery arrangement, heating chamber, and outlet port. As a result of such an arrangement, the aerosol delivery device 100 is configured to be customizable for each consumer, when multiple consumers are using the aerosol delivery device 100 simultaneously, such that each consumer is able to choose his or her own aerosol precursor composition 108 (e.g., a menthol, a crema, etc.,) for an individualized experience.

In other such aspects, for example, two different aerosol precursor compositions 108A-B contained within the respective reservoirs 128A-B are simultaneously delivered to a same heating chamber 106 such that the two different aerosol precursor compositions 108A-B are combinable within the heating chamber 106 prior to, during, and/or after aerosolization. As a result of such an arrangement, the aerosol delivery device 100 is configured to be customizable for a single consumer or multiple consumers, such that combinations of various aerosol precursor compositions 108A-B result in a unique experience.

The reservoir 128 is configured as either a reusable reservoir, or a removable and disposable reservoir. In one example, the reservoir 128 is reusable such that additional quantities of the aerosol precursor composition 108 are added to the reservoir 128 when needed. In other examples, the reservoir 128 is removed upon use of all of the aerosol precursor composition 108 contained within. A new reservoir 128 containing additional quantities of an aerosol precursor composition is then engaged with the housing 102, where the reservoir 128 is a disposable reservoir or a refillable and reusable reservoir. Regardless, the reservoir 128 is engageable with the housing 102 via a threaded engagement, a press-fit engagement, a magnetic engagement, etc. Otherwise, the reservoir 128 is fixedly engaged with the housing 102 such that the reservoir 128 is unable to be removed from the housing 102 (i.e., in the case of a refillable or a reusable reservoir). Regardless, the reservoir 128 is in fluid communication with the aerosol precursor delivery arrangement 126 such that the aerosol precursor composition(s) 108 is delivered to the heating chamber(s) 106 therefrom.

In order to meter a quantity of the aerosol precursor composition(s) 108 delivered to the heating chamber(s) 106, one embodiment of the reservoir 128 comprises a screen 130 having a grid composition fine enough to prevent all of the aerosol precursor composition 108 from being delivered to the heating chamber 106 at one time, but large enough to allow the composition particles to flow through at a limited rate. For example, as illustrated in FIG. 1, the screen 130 is configured to span a substantial entirety or an entirety of an interior diameter of the housing 102 and is disposed adjacent to the reservoir 128. In another example, as illustrated in FIG. 3, the screen 130 is disposed adjacent to both reservoirs 128A-B; although a screen for each respective reservoir 128A-B is also contemplated.

In some aspects, aerosol precursor composition 108, which may also be referred to as a vapor precursor composition, comprises one or more different components. The different components of the aerosol precursor composition 108 are selected from the group consisting of a liquid, a gel, a solid, a capsule, a colloid, a suspension, a botanical, and a combination thereof interspersed in a porous matrix or in a discrete packet (e.g., substrate). In some non-limiting examples, one of the components of the aerosol precursor composition 108 includes a polyhydric alcohol (e.g., glycerin, propylene glycol, or a mixture thereof). Representative types of further aerosol precursor compositions are set forth in U.S. Pat. No. 4,793,365 to Sensabaugh, Jr. et al.; U.S. Pat. No. 5,101,839 to Jakob et al.; PCT WO 98/57556 to Biggs et al.; and Chemical and Biological Studies on New Cigarette Prototypes that Heat Instead of Burn Tobacco, R. J. Reynolds Tobacco Company Monograph (1988); the disclosures of which are incorporated herein by reference.

The components of the aerosol precursor composition 108 are combined based on particular effects each component lends to the overall experience for the consumer. In some aspects, components that enable the aerosol delivery device 100 to provide some or all of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe are selected. In other aspects, components that enable the aerosol delivery device 100 to produce a uniformly heated aerosol 114 from the aerosol precursor composition 108 are also selected. For example, a component that prevents superheating of the aerosol precursor composition 108, such as inert, non-volatile granules (e.g., boiling chips) or other nucleation surfaces capable of absorbing excess microwave radiation 112, are selectable for the aerosol precursor composition 130. Alternatively, the controller element 132 is configured to selectively control the microwave radiation emitting device 110 to emit microwave radiation 112 at a frequency specific to one or more components of the aerosol precursor composition 108.

Some embodiments of the aerosol delivery device 100 include a controller element 132 in communication between the microwave radiation emitting device 110 and a sensing element 134 in communication with the aerosol precursor composition 108 within the heating chamber 106. The controller element 132 comprises, in some aspects, a microcontroller. The sensing element 134 comprises, in some aspects, a fiber optic probe. As illustrated in FIG. 1 and in more detail in FIG. 2A, the controller element 132 is disposed within the enclosure 104 and the sensing element 134 is disposed within the heating chamber 106. In another example, as illustrated in FIG. 2B, a single controller element 132 is in communication between the microwave radiation emitting device 110 and both sensing elements 134A and 134B disposed in respective heating chambers 106A-B.

In some embodiments, the sensing element(s) 134 is configured to sense a temperature, airflow velocity, pressure, aerosol precursor composition elements, or any combination thereof of the aerosol precursor composition 108 within the heating chamber 106. For example, where the sensing element 134 is configured to sense a temperature, the controller element 132 is responsive to the sensed temperature to regulate the microwave radiation 112 to heat the aerosol precursor composition 108 to only a maximum desired temperature. In this manner, the controller element 132 taken in conjunction with the sensing element(s) 134 is configured to prevent superheating, underheating, etc., of the aerosol precursor composition 108.

In other embodiments, the sensing element(s) 134 is also configured to sense a volume of the quantity of aerosol precursor composition 108 contained in the heating chamber 106. For example, where there are two heating chambers 106A-B, the sensing elements 134A-B are each configured to sense a capacity of the aerosol precursor composition 108 within a respective heating chamber 106A-B. The controller element 132 is responsive to the sensed capacity to prevent the aerosol precursor delivery arrangement 126 from directing any more of the aerosol precursor composition 108 to one or both of the heating chambers 106A-B, where one or both of the heating chamber 106A-B are at maximum capacity. As such, for example, a valve mechanism in communication with the controller element 132 is configured to limit a quantity of aerosol precursor composition 108 delivered to one or both of the heating chambers 106A-B. Alternatively, in instances where one of the heating chambers 106A-B is at maximum capacity, the controller 132 is responsive to the sensed maximum capacity of that chamber to direct the aerosol precursor composition 108 to the other heating chamber 106A-B not at maximum capacity.

Additionally, in various embodiments, an aerosol precursor composition transport element is disposed in the heating chamber 106 in communication with the aerosol precursor composition 108. For example and as illustrated in FIGS. 2A-B, one embodiment of the aerosol precursor composition transport element comprises a wick 136 formed from a variety of materials (e.g., cotton and/or fiberglass) configured to transport (i.e., absorb and wick) the aerosol precursor composition 108. Due to the material design of the wick, the wick 136 is configured to absorb a limited quantity (i.e., puff size amount) of the aerosol precursor composition 108 delivered to the heating chamber 106; the wick having the liquid absorbed thereby is then heated by the microwave radiation emitting device 110 to produce an aerosol 114. Additionally, for example, a puff sized amount of the aerosol precursor composition 108 is able to be pumped, dripped, or otherwise delivered to the heating chamber 106 and onto the wick 136. However, implementation of the wick 136 is optional.

Accordingly, in use, when a consumer draws on the mouthpiece element 122 of the aerosol delivery device 100, a quantity of the aerosol precursor composition 108 is directed, by the aerosol precursor delivery arrangement 126, from the reservoir 128 to the heating chamber 106. Alternatively, the aerosol precursor composition 108 is already disposed within the heating chamber 106 prior to the draw. The microwave radiation emitting device 110 is then activated (e.g., such as via a puff sensor or sensing element 134) and the components of the aerosol precursor composition 108 are vaporized or aerosolized within the heating chamber 106. In some aspects, the controller element 132 is communicatively connected with the microwave radiation emitting device 110 to control the microwave radiation 112 emitted therefrom. For example, where the sensing element 134 senses an aerosol precursor composition 108 within the heating chamber 106 requiring increased microwave radiation 112 to aerosolize (e.g., due to a temperature, volume, pressure, etc., of the aerosol precursor composition), the controller element 132 is able to control the microwave radiation emitting device 110 to emit microwave radiation 112 sufficient to aerosolize the aerosol precursor composition 108.

Drawing upon the mouthpiece element 122 of the aerosol delivery device 100 also causes ambient air to enter the airflow channel 120 and pass into the heating chamber 106. The drawn ambient air combines with the formed vapor/aerosol within the heating chamber 106 and/or the aerosol delivery arrangement 126 to transport an aerosol 114. The formed aerosol 114 is drawn from the heating chamber 106, passes through the aerosol delivery arrangement 126, out the outlet port 118, through the hose member 124, and out the mouthpiece element 122 of the device 100. In some aspects, any aerosol 114 that is not drawn though the outlet port 118 resides or remains within the aerosol delivery arrangement 126, where it is aged.

An exemplary mechanism that provides puff-actuation capability includes a Model 163PC01D36 silicon sensor, manufactured by the MicroSwitch division of Honeywell, Inc., Freeport, Ill. Still further components are optionally utilized in the aerosol delivery device 100 of the present disclosure. For example, U.S. Pat. No. 5,261,424 to Sprinkel, Jr. discloses piezoelectric sensors that can be associated with the mouth-end of a device to detect user lip activity associated with taking a draw and then trigger heating; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 by Fernando et al. discloses computer interfacing means for smoking devices to facilitate charging and allow computer control of the device; U.S. Pat. No. 8,689,804 by Fernando et al. discloses identification systems for smoking devices; and WO 2010/003480 by Flick discloses a fluid flow sensing system indicative of a puff in an aerosol generating system; all of the foregoing disclosures being incorporated herein by reference in their entireties.

Further description of other control components, including microcontrollers that can be useful in the present smoking article, are provided in U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., and U.S. Pat. No. 7,040,314 to Nguyen et al., all of which are incorporated herein by reference in their entireties.

FIGS. 4A-4C illustrate schematics of exemplary aerosol precursor processing units. An aerosol precursor processing unit is configured to pre-heat the aerosol precursor composition 108 prior to aerosolization of the aerosol precursor composition 108 by the device 100. Alternatively, the aerosol precursor processing unit is configured to process the aerosol precursor composition 108 after pre-heating of the aerosol precursor composition 108 by the device 100.

Referring to FIG. 4A, an aerosol precursor processing unit 400A is illustrated. The aerosol precursor processing unit 400A is configured to be in fluid communication with the heating chamber(s) 106. More particularly, the aerosol precursor processing unit 400A is configured to deliver the processed aerosol precursor composition to the heating chamber(s) via an outlet (not shown) communicating with the heating chamber(s) 106, through the airflow channel (e.g., 120, FIGS. 2A-B), or through the aerosol precursor delivery arrangement (e.g., 126, FIG. 1). The aerosol precursor processing unit 400A is configured to pre-heat the aerosol precursor composition 108 to a pre-heat temperature, the pre-heat temperature being less than a maximum desired temperature for forming the aerosol from the aerosol precursor composition 108, prior to the processed (i.e., pre-heated) aerosol precursor composition being delivered to the heating chamber(s) 106. Alternatively, the aerosol precursor composition 108 is pre-heated in the heating chamber(s) 106 of the aerosol delivery device 100 and removed from the heating chamber(s) 106 prior to vaporization/aerosolization of the aerosol precursor composition 108. At this point, the pre-heated aerosol precursor composition 108 is delivered (e.g., via the aerosol precursor delivery arrangement 126) to the aerosol precursor processing unit 400A and vaporized. Ambient air provided via an inlet (not shown) in the aerosol precursor processing unit 400A combines with the vaporized/aerosolized aerosol precursor composition transports the aerosol to be consumed by a user.

In some aspects, the aerosol precursor processing unit 400A comprises a heating element or an aerosol forming element configured to interact with the aerosol precursor composition provided therein. In one example, a heating element comprises a hot plate. In another example, a heating element comprises a coil heater 402. The coil heater 402 is configured as a resistive heating element that produces heat when electrical current is applied therethrough. Example materials from which the heating element 402 is formed include Kanthal (FeCrAl), Nichrome, molybdenum disilicide ($MoSi_2$), molybdenum silicide (MoSi), molybdenum disilicide doped with aluminum ($Mo(Si,Al)_2$), and ceramics (e.g., a positive temperature coefficient ceramic). In order to produce heat, the heating element 402 comprises conductive heater terminals (e.g., positive and negative terminals) that are configured to direct current flow through the heating element 402 and also for attachment to appropriate wiring or circuitry (not illustrated) to form an electrical connection of the heating element 402 with a battery or other electrical power source. In other non-limiting examples, the heating element 402 is non-electric and produces heat for vaporizing the aerosol precursor composition 108 via conduction, convection, and/or radiation.

In other aspects, the aerosol precursor processing unit 400A comprises a microwave radiation emitting device that is configured to interact with the aerosol precursor composition provided therein and pre-heat the aerosol precursor composition using emitted microwave radiation.

A sensing element 404 provided within the aerosol precursor processing unit 400A is configured to sense when the aerosol precursor composition 108 has been heated by the heating element 402 to the pre-heat temperature. The electrical connection with the heating element 402 is disengaged after the sensing element 404 senses that the pre-heat temperature is reached. Additionally, where the aerosol precursor composition is pre-heated in the heating chamber(s) 106 of the device 100, the sensing element 404 is configured to sense when a maximum temperature is reached and the heating element 402 is, subsequently, disengaged.

Referring now to FIG. 4B, an aerosol precursor processing unit 400B is illustrated. The aerosol precursor processing unit 400B is configured to be in fluid communication with the heating chamber(s) 106. More particularly, the aerosol precursor processing unit 400B is configured to deliver the processed aerosol precursor composition to the heating chamber(s) 106 via an outlet (not shown) communicating with the heating chamber(s) 106, through the airflow channel (e.g., 120, FIGS. 2A-B), or through the aerosol precursor delivery arrangement (e.g., 126, FIG. 1). The aerosol precursor processing unit 400B is configured to pre-heat a substrate material 406 having the aerosol precursor composition 108 associated therewith to a pre-heat temperature, the pre-heat temperature being less than a maximum desired temperature for forming the aerosol from the aerosol precursor composition 108, prior to the pre-heated substrate material 406 being delivered to the heating chamber 106.

In some aspects, the aerosol precursor processing unit 400B comprises a conventional microwave oven. The aerosol precursor processing unit 400B, thus, pre-heats the substrate 406 to the pre-heat temperature using the control and/or sensing components provided in conventional microwave ovens. The pre-heated substrate 406 is then delivered to the heating chamber 106 for aerosolization via further microwave radiation. Alternatively, the substrate 406 is delivered to the reservoir 128 and the aerosol precursor delivery arrangement 126 delivers limited quantities thereof to the heating chamber 106.

FIG. 4C illustrates an aerosol precursor processing unit 400C. The aerosol precursor processing unit 400C is configured to be in fluid communication with the heating chamber(s) 106. More particularly, the aerosol precursor processing unit 400C is configured to deliver the processed aerosol precursor composition to the heating chamber(s) 106 via an outlet (not shown) communicating with the heating chamber(s) 106, through the airflow channel (e.g., 120, FIGS. 2A-B), or through the aerosol precursor delivery arrangement (e.g., 126, FIG. 1). The aerosol precursor processing unit 400C is configured to pre-heat a membrane 408 comprising the aerosol precursor composition 108 to a pre-heat temperature, the pre-heat temperature being less than a maximum desired temperature for forming the aerosol from the aerosol precursor composition 108, prior to the pre-heated membrane 408 being delivered to the heating chamber 106.

In some aspects, the aerosol precursor processing unit 400C comprises a conventional microwave oven, while the membrane 408 comprises a single or a multi-use membrane. In one example, the aerosol precursor composition 108 is provided in the membrane 408; the membrane 408 is sealed, and then provided to the aerosol precursor processing unit 400C. The aerosol precursor processing unit 400C, thus, pre-heats the membrane 408 to the pre-heat temperature using the control and/or sensing components provided in conventional microwave ovens. The membrane 408 is provided to the aerosol precursor processing unit 400C in a deflated state, but transitions to an inflated state as the aerosol precursor composition 108 within is vaporized/aerosolized. The pre-heated, inflated membrane 408 is then able to be puffed on via a mouthpiece attachment or otherwise attached to the aerosol delivery device 100 in order to allow the aerosol to be delivered to a consumer in a controlled manner. After delivery of the aerosol, the membrane 408 is either disposed of (i.e., single-use) or is unsealed and an additional quantity of the aerosol precursor composition 108 is disposed within (i.e., multi-use).

In a further embodiment, not illustrated, the aerosol delivery device 100 is utilized to further evaporate an aerosol produced by another mechanism. More particularly, the microwave radiation emitting device 110 is configured to reduce in size aerosol particles produced by other mechanisms in order to make the particles small enough (e.g., 2 microns in diameter) for inhalation. Some such mechanisms for producing an aerosol include ink jet spray devices, which, in various embodiments, are configured to spray aerosol particles within an interior of the heating chamber 106 of the aerosol delivery device 100. For example, a thermal printer or a bubble jet printer is capable of spraying an aerosol particle approximately 4-40 microns in diameter, while a piezoelectric printer is capable of spraying an aerosol particle approximately 1-2 microns in diameter. As an aerosol comprised of particles larger than 2 microns is generally not conveniently inhalable, the sprayed aerosols are further evaporated by the microwave radiation emitting device 110 to reduce the size of the particles to an inhalable diameter, for example 2 microns or less.

Alternatively, a wick and/or coil arrangement is provided within an interior of the heating chamber 106 to produce an aerosol comprised of particles having individual diameters between approximately 200-500 nanometers. While an aerosol comprising particles of this diameter is inhalable, in some embodiments, the microwave radiation emitting device 110 is configured to further vaporize/aerosolize the aerosol 114.

Referring now to FIG. 5, a method of making an aerosol delivery device is illustrated. The method, generally designated 500, is utilized to make an aerosol delivery device that produces an aerosol by microwave radiation of a precursor composition, such as the one described above.

In step 502, a microwave radiation emitting device (e.g., 110, FIG. 1) is operably engaged with a heating chamber (e.g., 106, FIG. 1) configured to receive an aerosol precursor composition (e.g., 108, FIG. 1) therein. In some embodiments, the microwave radiation emitting device is configured to heat the aerosol precursor composition with microwave radiation emitted thereby to form an aerosol from the aerosol precursor composition. An aerosol precursor composition is disposed in a heating chamber In step 504, the heating chamber is engaged with a housing (e.g., 102, FIG. 1) having an outlet port (e.g., 118, FIG. 1) such that the outlet port is in fluid communication with the heating chamber, and such that the heating chamber is responsive to a suction applied to the outlet port for the aerosol to be drawn through the outlet port outwardly from the housing.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device, comprising:
   a heating chamber having an aerosol precursor composition disposed therein;
   a microwave radiation emitting device comprising a magnetron extending at least partially about and operably engaged with the heating chamber, the magnetron being configured to emit microwave radiation to heat the aerosol precursor composition therein with the microwave radiation, to form an aerosol from the aerosol precursor composition; and
   a housing having an outlet port and being in fluid communication with the heating chamber, the heating chamber being responsive to a suction applied to the outlet port for the aerosol to be drawn through the outlet port outwardly from the housing, wherein the outlet port includes an airflow shielding element configured to contain the microwave radiation within the heating chamber.

2. The device of claim 1, further comprising an aerosol precursor delivery arrangement operably engaged with the heating chamber and configured to direct the aerosol precursor composition to the heating chamber from a reservoir configured to contain the aerosol precursor composition therein and in fluid communication with the aerosol precursor delivery arrangement.

3. A method of making an aerosol delivery device, the method comprising:
   operably engaging a microwave radiation emitting device with a heating chamber configured to receive an aerosol precursor composition therein, the microwave radiation emitting device comprising a magnetron extending at least partially about the heating chamber and being configured to heat the aerosol precursor composition with microwave radiation emitted thereby to form an aerosol from the aerosol precursor composition; and engaging the heating chamber with a housing having an outlet port such that the outlet port is in fluid communication with the heating chamber, and such that the heating chamber is responsive to a suction applied to the outlet port for the aerosol to be drawn through the outlet port outwardly from the housing, wherein the outlet port includes an airflow shielding element configured to contain the microwave radiation within the heating chamber.

4. The device of claim 1, wherein the magnetron is disposed within an enclosure configured to substantially surround the heating chamber.

5. The device of claim 4, further comprising two or more reservoirs, wherein each reservoir is configured to contain a distinct aerosol precursor composition therein, wherein each of the two or more reservoirs is in fluid communication with the aerosol precursor delivery arrangement and co-operable therewith for the aerosol precursor delivery arrangement to direct any of the distinct aerosol precursor compositions from the respective one of the two or more reservoirs to the heating chamber.

6. The device of claim 5, further comprising an airflow channel defined within the housing or the enclosure, and configured to allow airflow between the heating chamber and ambient air external to the housing or the enclosure.

7. The device of claim 6, wherein the airflow channel includes an airflow shielding element configured to cooperate with the enclosure to contain the microwave radiation within the enclosure.

8. The device of claim 1, comprising a hose member having engaging proximal end engaged with the outlet port and an opposing distal end engaged with a mouthpiece element, the mouthpiece element and the hose member being in fluid communication with the heating chamber via the outlet port so as to receive the aerosol therefrom in response to suction applied to the mouthpiece element.

9. The device of claim 1, comprising a controller element in communication between the microwave radiation emitting device and a sensing element in communication with the aerosol precursor composition within the heating chamber, the sensing element being configured to sense a temperature of the aerosol precursor composition within the heating chamber, the controller element being responsive to the sensed temperature to regulate the microwave radiation output by the magnetron to heat the aerosol precursor composition within the heating chamber to a maximum desired temperature.

10. The device of claim 1, wherein the aerosol precursor composition is selected from the group consisting of a liquid, a gel, a solid, a capsule, a colloid, a suspension, a botanical, and a combination thereof.

11. The device of claim 10, wherein one component of the aerosol precursor composition is configured to prevent superheating of the aerosol precursor composition.

12. The device of claim 1, comprising a wick engaged with the heating chamber, the wick being in communication with the aerosol precursor composition, wherein the magnetron is configured to heat the wick such that an amount of the aerosol formed thereby is proportional to the an amount of the aerosol precursor composition wicked by the wick.

13. The device of claim 1, wherein the heating chamber comprises a first heating sub-chamber and a second heating sub-chamber, one of the first and second heating sub-chambers having a greater capacity for the aerosol precursor composition than the other, and wherein the first and second heating sub-chambers are in fluid communication with the outlet port via a selector element, the selector element being responsive to the suction applied through the outlet port to direct the aerosol to the outlet port from the selected one of the first and second heating sub-chambers, an amount of the aerosol corresponding to a magnitude of the suction.

14. The device of claim 1, comprising an aerosol precursor processing unit in fluid communication with the heating chamber and configured to pre-heat the aerosol precursor composition to a pre-heat temperature, the pre-heat temperature being less than a maximum desired temperature for forming the aerosol from the aerosol precursor composition, prior to the pre-heated aerosol precursor composition being directed to the heating chamber.

15. The device of claim 14, wherein the aerosol precursor processing unit comprises a heating element or an aerosol forming element configured to interact with the aerosol precursor composition.

16. The device of claim 1, comprising an aerosol precursor processing unit in communication with the heating chamber and configured to pre-heat a substrate material having the aerosol precursor composition associated therewith to a pre-heat temperature, the pre-heat temperature being less than a maximum desired temperature for forming the aerosol from the aerosol precursor composition, prior to the pre-heated substrate material being directed to the heating chamber.

17. The device of claim 1, comprising an aerosol precursor processing unit in communication with the heating chamber and configured to pre-heat a membrane comprised of the aerosol precursor composition to a pre-heat temperature, the pre-heat temperature being less than a maximum desired temperature for forming the aerosol from the aerosol precursor composition, prior to the pre-heated membrane being directed to the heating chamber.

18. The method of claim 3, further comprising engaging an aerosol precursor processing unit in fluid communication with the heating chamber, the aerosol precursor processing unit being configured to pre-heat a substrate material having the aerosol precursor composition associated therewith to a pre-heat temperature, the pre-heat temperature being less than a maximum desired temperature for forming the aerosol from the aerosol precursor composition, prior to the pre-heated substrate material being directed to the heating chamber.

19. The method of claim 3, further comprising engaging an aerosol precursor delivery arrangement in fluid communication with the heating chamber, the aerosol precursor delivery arrangement being configured to direct the aerosol precursor composition to the heating chamber from a reservoir having the aerosol precursor composition therein.

20. The method of claim 3, further comprising engaging an aerosol precursor processing unit in fluid communication with the heating chamber, the aerosol precursor processing unit being configured to pre-heat a membrane comprising of the aerosol precursor composition to a pre-heat temperature, the pre-heat temperature being less than a maximum desired temperature for forming the aerosol from the aerosol precursor composition, prior to the pre-heated membrane being directed to the heating chamber.

21. The method of claim 3, further comprising disposing the magnetron within an enclosure configured to substantially surround the heating chamber.

22. The method of claim 21, further comprising forming two or more reservoirs within the housing, wherein each reservoir includes a distinct aerosol precursor composition therein, wherein each of the two or more reservoirs is in fluid communication with the aerosol precursor delivery arrangement and is co-operable therewith for the aerosol precursor delivery arrangement to direct any of the distinct aerosol precursor compositions from the respective one of the two or more reservoirs to the heating chamber.

23. The method of claim 22, further comprising defining an airflow channel within the housing or the enclosure, the airflow channel being configured to allow airflow between the heating chamber and ambient air external to the housing or the enclosure.

24. The method of claim 23, further comprising disposing an airflow shielding element in the airflow channel, the airflow shielding element being configured to cooperate with the enclosure to contain the microwave radiation within the enclosure.

25. The method of claim 3, further comprising engaging a proximal end of a hose member with the outlet port and engaging an opposing distal end of the hose member with a mouthpiece element, the mouthpiece element and the hose member being in fluid communication with the heating chamber via the outlet port so as to receive the aerosol therefrom in response to suction applied to the mouthpiece element.

26. The method of claim 3, further comprising operably engaging a controller element between the microwave radiation emitting device and a sensing element in communication with the aerosol precursor composition within the heating chamber, the sensing element being configured to sense a temperature of the aerosol precursor composition within the heating chamber, and the controller element being configured to be responsive to the sensed temperature to regulate the microwave radiation output by the magnetron to heat the aerosol precursor composition within the heating chamber to a maximum desired temperature.

27. The method of claim 3, further comprising selecting the aerosol precursor composition from the group consisting of a liquid, a gel, a solid, a capsule, a colloid, a suspension, a botanical, and a combination thereof.

28. The method of claim 27, wherein selecting the aerosol precursor composition further comprises selecting the aerosol precursor composition such that one component thereof is configured to prevent superheating of the aerosol precursor composition.

29. The method of claim 3, further comprising engaging a wick with the heating chamber such that the wick is in communication with the aerosol precursor composition, wherein the magnetron is configured to heat the wick such that an amount of the aerosol formed thereby is proportional to the an amount of the aerosol precursor composition wicked by the wick.

30. The method of claim 3, further comprising defining, in the heating chamber, a first heating sub-chamber and a second heating sub-chamber, one of the first and second heating sub-chambers having a greater capacity for the aerosol precursor composition than the other, and wherein the first and second heating sub-chambers are configured to selectively be in fluid communication with the outlet port via a selector element, the selector element being responsive to the suction applied through the outlet port to direct the aerosol to the outlet port from the heating sub-chamber in selective communication therewith, an amount of the aerosol corresponding to a magnitude of the suction.

31. The method of claim 3, further comprising engaging an aerosol precursor processing unit in fluid communication with the heating chamber, the aerosol precursor processing unit being configured to pre-heat the aerosol precursor composition to a pre-heat temperature, the pre-heat temperature being less than a maximum desired temperature for forming the aerosol from the aerosol precursor composition, prior to the pre-heated aerosol precursor composition being directed to the heating chamber.

32. The method of claim 31, wherein engaging the aerosol precursor processing unit comprises arranging a heating element or an aerosol forming element to interact with the aerosol precursor composition prior to the pre-heated aerosol precursor composition being directed to the heating chamber.

* * * * *